United States Patent [19]

Milbrath

[11] Patent Number: 4,977,080
[45] Date of Patent: Dec. 11, 1990

[54] CHEMILUMINESCENT METHODS AND A KIT THEREFOR INVOLVING A BETA-LACTAM

[75] Inventor: Dean S. Milbrath, Oakdale, Minn.

[73] Assignee: Minnesota Mining and Manufacturing Co., St. Paul, Minn.

[21] Appl. No.: 12,425

[22] Filed: Feb. 9, 1987

Related U.S. Application Data

[63] Continuation of Ser. No. 597,483, Apr. 6, 1984, abandoned.

[51] Int. Cl.$^5$ ............................................... C12Q 1/28
[52] U.S. Cl. ...................................... 435/28; 435/184; 436/92; 436/96; 436/172; 422/52; 422/61
[58] Field of Search ...................... 435/4, 28, 184, 810; 436/92, 96, 172; 422/61, 52; 425/18, 32

[56] References Cited

U.S. PATENT DOCUMENTS

| | | | |
|---|---|---|---|
| 4,181,650 | 1/1980 | Maier, Jr. .............................. | 436/18 |
| 4,220,450 | 9/1980 | Maggio ................................ | 436/537 |
| 4,478,817 | 10/1984 | Campbell et al. ...................... | 435/7 |
| 4,598,044 | 7/1986 | Kricka et al. ......................... | 435/28 |
| 4,764,462 | 8/1988 | Bredehorst et al. ................... | 435/18 |

OTHER PUBLICATIONS

Hardy et al., *Talanta*, 1977, 24, 297–302.

*Primary Examiner*—Esther L. Kepplinger
*Assistant Examiner*—Carol A. Spiegel
*Attorney, Agent, or Firm*—Donald M. Sell; Walter N. Kirn; Robert W. Sprague

[57] ABSTRACT

Methods for the detection and measurement of compounds containing beta-lactam rings by chemiluminescence of the compounds in the presence of a chemiluminescent compound such as luminol, and for improving the sensitivity of assays using chemiluminescent reactions such as the luminol reaction utilizing compounds containing beta-lactam rings are described. A kit for conducting such chemiluminescent assays is also described.

7 Claims, 5 Drawing Sheets

CHEMILUMINESCENT METHODS AND A KIT THEREFOR INVOLVING A BETA-LACTAM

This is a continuation of application Ser. No. 597,483, filed Apr. 6, 1984, now abandoned.

TECHNICAL FIELD

The present invention relates to a method for detecting beta-lactams in samples, and to a method for detecting components of chemiluminescent reactions. The present invention also relates to an assay kit for conducting certain of these assays.

BACKGROUND OF THE INVENTION

A few chemical compounds exhibit chemiluminescent behavior, and they are generally valued for this property. Luminol (5-amino-2,3-dihydro-1,4-phthalazinedione) is well known for its ability to emit light when oxidized. It is used in a number of analytical methods, for example, to analyze for trace metal ions, copper, iron, peroxides and cyanides.

The light emission of luminol is typically elicited by combining it with an oxidizing agent such as hydrogen peroxide in the presence of a catalyst for an oxidation reaction such as a peroxidase. This reaction is called the "luminol reaction" herein. It has been reported by Whitehead, et al., *Nature,* 305, 158–159 (1983) that the addition of firefly luciferin to a luminol reaction causes enhanced light output.

Assays using chemically induced fluorescence are known to the art, for example, see U.S. Pat. No. 4,220,450.

U.S. Pat. No. 4,433,060 discloses a chemiluminescent immunoassay utilizing a triphenylmethane dye activated by a peroxide and chloramine. The triphenylmethane dye is used as a labelling substance.

Yurow et al, *Analytica Chimica Acta,* 68, pp. 203–204 (1974), discloses an assay for certain ketones employing a chemiluminescence reaction involving luminol.

No reports of fluorescence or chemiluminescence by beta-lactams are known.

SUMMARY OF THE INVENTION

The present invention relates to the use of beta-lactams as compounds which enhance the chemiluminescence of reactions such as the luminol reaction. More specifically, the chemiluminescent behavior of beta-lactams in conjunction with luminol and other chemiluminescent compounds is useful in the luminescent detection of specific beta-lactams, particularly antibiotics containing a beta-lactam ring structure, and in the qualitative and quantitative measurement of these beta-lactams. The invention also relates to improving assays based on chemiluminescent reactions (such as the luminol reaction) as a result of increasing the sensitivity of the reaction by using a beta-lactam. The invention also relates to simplifying chemiluminescent reactions by reducing or eliminating the need for an oxidation catalyst. Finally, the present invention also relates to a kit for conducting chemiluminescent assays.

More particularly, one method of the invention for detecting a beta-lactam in a sample comprises the steps of (a) combining together as a mixture (i) a reaction system comprising a chemiluminescent compound, a peroxide source and a base, and (ii) a predetermined portion of the sample being analyzed; and (b) measuring the light output of the mixture; the reaction system being further characterized as one which, if the predetermined portion of said sample contained, as the only beta-lactam, penicillin G in an amount such that the mixture contained penicillin G in a concentration of 0.45 mM, produces a light output signal which, when measured by a luminometer and integrated over 30 seconds beginning with the initiation of the signal, is at least about two times, and preferably at least about four times, that produced if the predetermined portion of the sample was free of beta-lactam. The reaction system may further comprise an oxidation catalyst for the chemiluminescent reaction.

Another method of the invention is one for detecting a beta-lactam in a sample comprising the steps of (a) combining together as a mixture (i) a reaction system comprising a chemiluminescent compound, a peroxide source and a base, and (ii) a predetermined portion of said sample, and (b) measuring the light output of said mixture; wherein the chemiluminescent compound is selected from the group consisting of luminol, a luminol analog, isoluminol, an isoluminol analog, coumarin 2, sulforhodamine 101, umbelliferone, 4-methylumbelliferone and fluorescein.

Still another method of the invention is one for enhancing the sensitivity of an assay reaction for the detection of a component of a chemiluminescent reaction involving a chemiluminescent compound, a peroxide source, and optionally an oxidation catalyst. The component being assayed for may be any of the foregoing. This method comprises including a beta-lactam in the assay reaction in order to increase the sensitivity thereof.

It has been found in the present invention that the enhanced light output of the chemiluminescent reaction caused by beta-lactams is generally synergistic rather than additive, that is, the total light output is greater than the sum of the light outputs of the individual reactants. For this reason, chemiluminescent reactions of the type described herein, namely, "beta-lactam reactions", provide powerful, very sensitive assay methods for beta-lactams, particularly beta-lactam antibiotics. Similarly, employment of a beta-lactam reaction in a chemiluminescent assay for a component of the beta-lactam reaction such as a chemiluminescent compound (e.g., luminol), a peroxide source, or an oxidation catalyst (e.g., horseradish peroxidase), provides a very sensitive assay method for such a component.

BRIEF DESCRIPTION OF THE DRAWING

Understanding of the invention will be enhanced by referring to the accompanying drawing in which:

FIG. 1 is a plot of beta-lactam concentration versus light output obtained using a method of the present invention (see Example 3 below);

FIG. 2 is a plot of time versus light output using a method of the present invention (see Example 4 below);

FIG. 3 is an illustration of characteristic traces for particular beta-lactams obtained using a method of the present invention (see Example 5 below);

FIG. 4 is a plot of luminol concentration versus light output obtained using a method of the present invention (see Example 9 below);

FIG. 5 is a plot of hydrogen peroxide concentration versus light output obtained using a method of the present invention (see Example 10 below);

FIG. 6 is a plot of penicillin concentration in plasma versus light output obtained using a method of the present invention (see Example 12 below);

FIG. 7 is a plot of penicillin concentration in raw milk versus light output obtained using a method of the present invention (see Example 12 below);

FIG. 8 is a plot of time versus light output obtained using a method of the present invention (see Example 13 below); and FIG. 9 is a plot of horseradish peroxidase concentration versus light output obtained using a method of the present invention (see Example 16 below).

DETAILED DESCRIPTION

The present invention describes novel reactions and compositions which exhibit chemiluminescent behavior and the utilization of the novel reactions and compositions as analytical assay tools.

As used throughout the instant specification and claims, the term "beta-lactam" designates compounds containing a ring.

The presence of a signal or label which can be measured in proportion to the amount of the substance assayed is an essential part of any quantitative diagnostic assay or analytical procedure. For the purposes of this invention, the signal which is measured is a light output. It has been found that beta-lactams, and particularly beta-lactam antibiotics, are mildly chemiluminescent when oxidized in the presence of an oxidation catalyst. This phenomenon in itself is surprising and useful. Surprisingly and unexpectedly, when a chemiluminescent reaction such as the luminol reaction is conducted in the presence of a beta-lactam, a synergistic chemiluminescent reaction occurs. This reaction has been found to be synergistic in that the light output is greater than the sum of the partial light outputs. The luminol reaction itself gave about 1000 relative light units under the conditions of Example 1. When only the beta-lactams were reacted under the conditions of Example 1, as shown in Example 2, mild chemiluminescence of up to 225 relative light units was observed. In runs B, C, D, E and F of Example 1, it was found that very large increases of light output can be obtained from the luminol reaction.

Chemiluminescent reactions such as the luminol reaction generally require the presence of a chemiluminescent compound (e.g., luminol in the luminol reaction), an oxidizing agent such as a peroxide, and may require an oxidizing catalyst such as a peroxidase. As indicated below, the presence of a beta-lactam in the beta-lactam reaction permits, in many instances, the elimination of the oxidation catalyst from the chemiluminescent reaction. Such elimination is desirable since the reaction system is simplified (i.e., due to the elimination of a component), and since an increase in sensitivity of the assay often results.

As used in the instant specification and claims, the phrase "chemiluminescent compound" designates a compound which accepts energy and emits it in the form of fluorescence in the presence of a peroxide (i.e., as the result of peroxide reaction with and/or decomposition in the presence of the chemiluminescent compound). Chemiluminescent compounds which may be used in the practice of the present invention include luminol and isoluminol; luminol and isoluminol analogs such as those described in U.S. Pat. Nos. 4,355,165 and 4,226,993, both patents being incorporated herein by reference; coumarin 2; fluorescein; fluoresceinamine isomer II; sulforhodamine 101; and umbelliferone and 4-methylumbelliferone.

As far as the peroxide source is concerned, it is believed that essentially any peroxide source which is useful in the luminol reaction would be useful in the instant beta-lactam reaction. Examples of suitable peroxide sources which may be used in the beta-lactam reaction include hydrogen peroxide; sodium perborate; organic peroxides such as m-chloroperbenzoic acid; and organic hydroperoxides such as tertiary butyl hydroperoxide.

Suitable oxidation catalysts for use in the present invention include peroxidases such as horseradish peroxidase; oxidizable metal ions in aqueous solution such as aqueous solutions containing $Co^{+2}$, $Fe^{+2}$, $Cu^+$, $Cr^{+3}$, $Ni^{+2}$ and other transition metal ions; microperoxidase (Sigma Chemical Co., St. Louis, Missouri); and metallo-porphyrintype compounds such as cobalamin, hemoglobin and hematin. In general it is believed that catalysts for the normal luminol reaction catalyze the synergized reaction of the present invention. In addition, it has been found that in many cases the synergistic reaction of the present invention may be carried out without the catalysts required for the luminol reaction or with reduced amounts of catalyst.

Beta-lactams which may be detected using the instant beta-lactam reaction or which may be used in an assay for detecting a chemiluminescent compound, a peroxide source, or an oxidation catalyst include penicillins such as penicillin G, penicillin V, ampicillin, cloxicillin and aminopenicilloic acid; and cephalosporins such as cephapirin and cephalothin.

The enhanced light output of the beta-lactam reaction of the invention varies depending upon the molar ratio of the chemiluminescent compound to beta-lactam. This is shown quantitatively in Examples 3 and 9 for luminol as the chemiluminescent compound. In Example 3, as low as 150 nanograms of penicillin G per milliliter is detected. The chemiluminescent reaction has been detected for amounts of beta-lactam as low as 100 nanograms per milliter. The sensitivity will depend upon the specific beta-lactam used and the reaction conditions employed.

In view of the observation that the luminol reaction shows a linear enhanced light output relative to the amount of beta-lactam present (Example 3), the reaction may be used to measure the concentration of beta-lactam present in a quantitative manner. This is done by including comparisons with standard curves. Since different beta-lactams exhibit different degrees of enhanced light output, it is necessary to prepare a different standard curve for each beta-lactam.

In order for the beta-lactam reaction to occur, the aqueous medium must be basic. That is, the pH should be greater than about 7.5, and is preferably in the range of about 7.5 to 12, and most preferably about 8.5 to 12. For the analysis of luminol, hydrogen peroxide or a beta-lactam, the preferred pH is about 10 to 12. The preferred pH for a specific chemiluminescent reaction of the invention will vary depending upon the nature of the reactants involved such as the type of beta-lactam. The reaction may be made basic using common organic or inorganic bases such as sodium bicarbonate, sodium hydroxide, glycine, sodium borate, sodium phosphate, imidazole, tris(hydroxymethyl)aminomethane, and the like, weaker bases being preferred.

Figure 2:
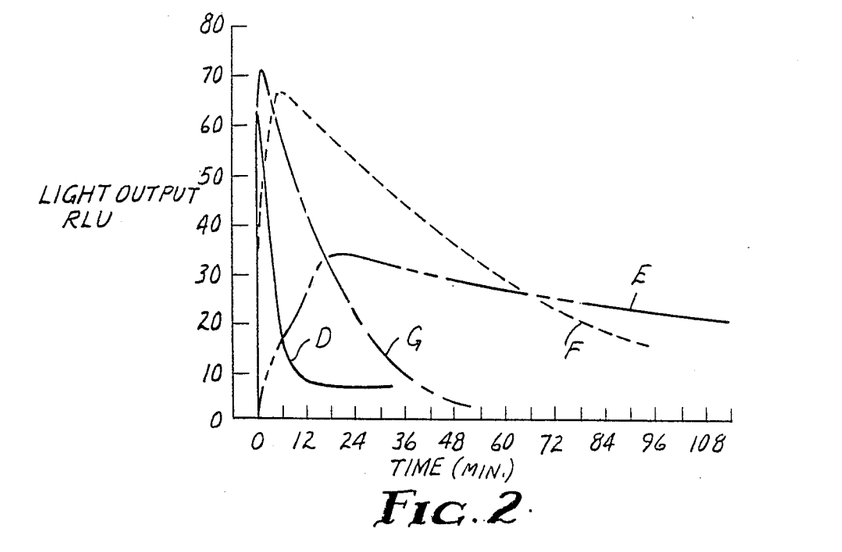

As indicated above, the heta-lactam reaction described herein is very useful for quantitative and qualitative analyses for beta-lactams, particularly beta-lactam antibiotics in liquid (e.g., aqueous) samples such as milk and plasma. Moreover, as discussed in Example 5 and shown in FIG. 2, each beta-lactam gives a different characteristic light output trace as recorded by a strip recorder coupled to a luminometer. Accordingly, these chemiluminescent "fingerprints" are useful as a qualitative analysis method.

When the beta-lactam reaction is used in a method for detecting a beta-lactam in a sample, the reaction system employed in such a method comprises a chemiluminescent compound, a peroxide source, a base and optionally an oxidation catalyst. In one such method of the invention, the reaction system is further characterized as one which, if the predetermined portion of the sample being assayed contained, as the only beta-lactam, penicillin G in an amount such that the complete reaction mixture contained penicillin G in a concentration of 0.45 mM, produces a light output signal which, when measured using a conventional luminometer and integrated over a 30 second period beginning with the initiation of the signal, is at least about two times that produced if the predetermined portion of the sample was free of beta-lactam. In order to determine whether a reaction system is suitable for use in this particular method, one performs the assay using the predetermined portion of a sample (that is, for example, plasma if it is plasma to be assayed using the method of the invention) which is known to contain no beta-lactam (e.g., as determined by another analytical method), and then again using the predetermined portion of the sample which is known to contain sufficient penicillin G to result in a concentration of penicillin G in the mixture (comprising the reaction system and the predetermined portion of sample) of.0.45 mM. The light output signals are determined using a luminometer and integrating over the first 30 seconds as described above, those signals then being compared. When determining whether a reaction system is suitable for use in this particular method, determination of the light output signals should be initiated within about 10 seconds of the time the sample and components of the reaction system are combined.

It is to be understood, of course, that the methods of the invention themselves may employ any suitable means for determining light output signal, that the light output signal can be analyzed by any suitable method such as by measuring peak height, integrating the area beneath the entire signal or a portion thereof, etc..

When practicing the methods of the invention for detecting a beta-lactam, the various components of the reaction system and the predetermined portion of the sample may be combined in any order.

The beta-lactam reaction described herein is also very useful in analytical assays for components of the beta-lactam reaction such as a chemiluminescent compound, a peroxide source or an oxidation catalyst.

The beta-lactam reaction described herein is also useful in analytical reactions wherein the label is a chemiluminescent compound (e.g., luminol) or a catalyst for the chemiluminescent reaction. These reactions are made more sensitive, that is, the component being assayed for is detected and more readily quantitated due to the greater light output resulting from the presence of the beta-lactam. Furthermore, the present invention now permits the use of beta-lactams as labels, for example, in ligand-antiligand binding assays which measure beta-lactam labeled species.

Examples of known luminol-based immunoassays are assays for steroids such as progesterone; for biotin and avidin; for thyroxine; and for hepatitis B surface antigen. These assays are described in the book "Luminescent Assays: Perspectives in Endocrinology and Clinical Chemistry" edited by M Serio and M. Pozzagli, Raven Press, New York, 1982.

Examples of luminol-reaction-based assays wherein the labeled species is horseradish peroxidase, microperoxidase, hemin or hemoglobin include protein binding assays, as described by Olsson et al., J. Immunological Methods, 25, 127–135 (1979); an assay for hemoglobin and enzyme immunoassays as described in the above mentioned "Luminescent Assays: Perspectives in Endocrinology and Clinical Chemistry"; and an assay based on a hemin catalyst label on human serum albumin as described in Analytical Chemistry, 54, 1126–1129 (1982).

The usefulness of the enhancement of chemiluminescent reactions as a method for improving assays can be explained more fully as follows: A chemiluminescent reaction requires or utilizes several substrates. One or more (generally all) of the substrates may be critical or rate-limiting. The substrates may be bound or unbound, i.e., in some cases substrates may be bond to other substances, for example, drugs, antibodies, proteins, antigens, DNA and the like, in order to provide a label by which such other substancies may be detected. In the example of the luminol reaction, free luminol or luminol, bound to some other substance may be detected. This reaction would be enhanced by the method of the invention.

Because peroxide source is a necessary component in the chemiluminescent reaction, the presence of the peroxide source may be shown by the occurrence of the chemiluminescent reaction. Thus, the method of the invention will enhance, for example, the detection of hydrogen peroxide or substrates that generate hydrogen peroxide. Similarly, the detection of beta-lactams, beta-lactams bonded to other substances, luminol-reaction catalysts and catalysts bonded to other substances may be improved by the method of the invention.

In view of the chemiluminescence of the beta-lactams, they can be used as labels in immunoassays. For example, all of the reactions of U.S. Pat. No. 4,220,450 which involve a chemiluminescent reaction which are enhanced by the presence of beta-lactams would offer opportunities for the use of the present invention, that is, the ligand or anti-ligand described in U.S. Pat. No. 4,220,450 could be labeled with a component of the chemiluminescent reaction, and the ligand or antiligand detected more readily as a result of enhancement of the chemiluminescent reaction using a beta-lactam.

As indicated above, employment of an oxidation catalyst is optional in the instant beta-lactam reaction. It also has been found that the addition to certain of those beta-lactam reactions described herein which involve an oxidation catalyst of an ascorbate salt (e.g., sodium ascorbate) or salts of certain ions which poison the oxidation catalyst increases the sensitivity of the chemiluminescent assay. Suitable ion salts include azide salts (e.g., sodium azide), and a mixture of an azide salt and a cyanide salt (e.g., the latter being sodium cyanide). A mixture of an ascorbate and an azide salt has also been found to be suitable. While not wishing to be bound by any theory, it is believed that two reactions are involved in the instant chemiluminescent reaction in which an oxidation catalyst such as horseradish peroxidase is present. One reaction is the conventional chemiluminescent reaction and the other is a different reaction which requires the presence of a beta-lactam. It is believed that sensitivity is increased in the presence of a poison of the oxidation catalyst due to a resulting decrease in the light output of the former reaction and/or an increase in the light output of the latter reaction.

The assay kits of the present invention for detecting a component of a chemiluminescent reaction comprise (i) the reactants of the chemiluminescent reaction other than the component to be assayed for; and (ii) a beta-lactam. Such reactants and beta-lactam are present in sufficient quantities to conduct a plurality of assays, and are packaged in substantially stable form (i.e., the kit exhibits a shelflife of at least about 30 days at room temperature).

The following Examples are offered by way of illustration and not by way of limitation.

EXAMPLE 1

A solution was prepared by combining 100 microliters of an aqueous solution which was 0.0020M in luminol, 0.0025M in ethylenediaminetetraacetic acid and 0.30M in sodium bicarbonate (pH 10.5), 100 microliters of a beta-lactam antibiotic ($2 \times 10^{-3}$ M) in water, and 100 microliters of an aqueous solution containing horseradish peroxidase (440 nanograms per milliter), bovine serum albumin (200 micrograms per milliliter) and 0.0050M ethylenediaminetetraacetic acid. The reaction was monitored using a Lumac® Biocounter 2010 (a luminometer available from 3M, St. Paul, MN). The reaction was then initiated by the addition of 100 microliters of 0.018M aqueous hydrogen peroxide which was 0.0010M in ethylenediaminetetraacetic acid. The light output was measured for a 30 second period following the initiation of the reaction and was recorded as a trace on a strip chart recorder and recorded and integrated by the luminometer. As a blank, the reaction was run substituting distilled water for the 100 microliters of solution containing the beta-lactam antibiotic.

Table I shows the light output measured by the luminometer, the calculated enhanced light output (abbreviated as ELO and representing recorded light output minus light output of blank) and enhanced light output factor (abbreviated as ELO Factor herein and representing light output divided by light output of blank). The units of light output are relative light units (abbreviated as RLU herein) as measured on the instrument.

TABLE I

| RUN | ANTIBIOTIC | LIGHT OUTPUT (RLU) | ELO (RLU) | ELO FACTOR |
|---|---|---|---|---|
| A | None | 977 | 0 | 1.0 |
| B | Penicillin G | 8698 | 7721 | 8.9 |
| C | Penicillin V | 12192 | 11215 | 12.5 |
| D | Ampicillin | 5592 | 4615 | 5.7 |
| E | Cephalothin | 3196 | 2219 | 3.3 |
| F | Aminopenicilloic Acid | 6231 | 5254 | 6.4 |
| G | Penicillamine | 1214 | 237 | 1.2 |
| H | Penicilloyl aminocaproate | 1717 | 740 | 1.8 |
| I | Gentamicin | 1072 | 95 | 1.1 |
| J | Chloramphenicol | 1230 | 253 | 1.3 |
| K | Tetracycline | 642 | (335) | −0.4 |

It is noted that in Runs B, C, D, E and F the beta-lactam antibiotics produced large increases of light from the reaction, varying from 230% in Run E to 1150% in Run C. Beta-lactam hydrolysis products (runs G and H) and non-lactam antibiotics (runs I, J, and K) did not produce comparably large increases in light output.

EXAMPLE 2

A solution was prepared by combining 100 microliters of water which was 0.30M in sodium carbonate (pH 10.5) and 0.0025M in ethylenediaminetetraacetic acid, 100 microliters of a beta-lactam antibiotic ($2 \times 10^{-3}$ M) in water, and 100 microliters of an aqueous solution containing horseradish peroxidase (440 nanograms per milliliter), bovine serum albumin (200 micrograms per milliliter) and ethylenediaminetetraacetic acid (0.0050M). The reaction was monitored using a luminometer, and was initiated by adding 100 microliters of an aqueous solution which was 0.018M in hydrogen peroxide and 0.0010M in ethylenediaminetetraacetic acid. The light output was measured for a 30 second period following the initiation of the reaction, and was recorded as a trace on a strip chart recorder and recorded and integrated by the luminometer.

Table II shows the light output measured by the luminometer when the indicated beta-lactam antibiotic was used.

TABLE II

| LIGHT OUTPUT OF BETA-LACTAM ANTIBIOTICS | |
|---|---|
| Antibiotic | Light Output (RLU) |
| Penicillin G | 225 |
| Penicillin V | 26 |
| Ampicillin | 82 |
| Cephalothin | 44 |
| Aminopenicilloic Acid | 113 |

These results demonstrate that all beta-lactam antibiotics tested showed mild chemiluminescence, although the total chemiluminescence varied significantly among the antibiotics under the conditions employed.

EXAMPLE 3

The beta-lactam reaction was used here to quantitate penicillin G, ampicillin, and cephalothin. Beta-lactam solutions (50 microliters), diluted in water, were added to 100 microliters of luminol solution, 0.1 mg/ml in 0.1 M sodium bicarbonate, 0.005 M ethylenediaminetetraacetic acid, and 0.1% Tween® 20 (a polyoxyethylene sorbitan monolaurate, available from ICI Americas, Wilmington, DE) at pH 11.0 (penicillin G), pH 12.0 (ampicillin), or pH 10.0 (cephalothin). The reaction was initiated by the addition of 100 microliters of tert-butyl hydroperoxide, 0.02 M in 0.001 M ethylenediaminetetraacetic acid, and the light produced by the reaction integrated over 1 minute intervals.

Figure 1:
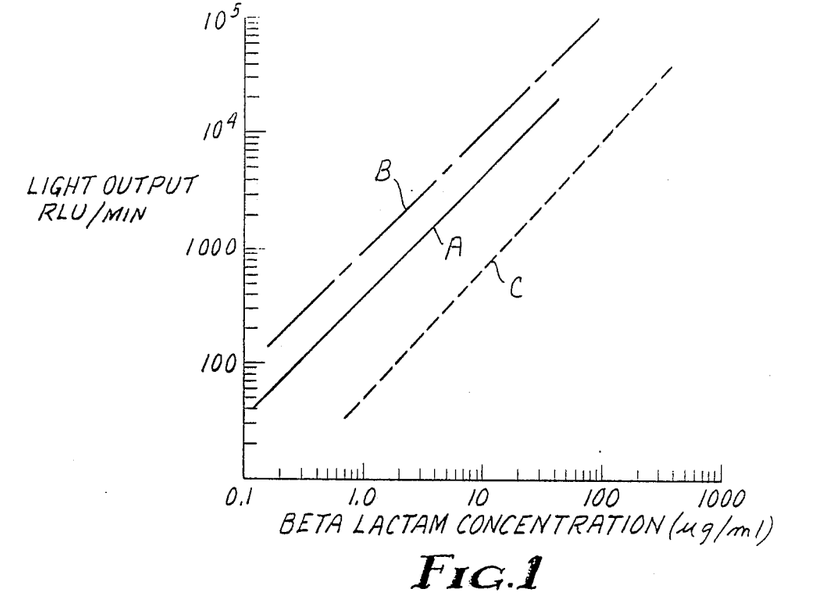

The light outputs at three, two and one minutes for penicillin G, ampicillin, and cephalothin, respectively, were plotted in FIG. 1 as curves A, B and C, respectively. These plots show that the light produced from these reactions is linearly related to the concentration of the particular beta-lactam antibiotic present in the reaction mixture. The approximate sensitivities of these assays are 150, 250 and 500 ng/ml, respectively, as determined by two times the standard deviation of the background reaction.

EXAMPLE 4

The light output from the beta-lactam reaction can be changed in both the amount of light output and the duration of the light output by choosing the appropriate reaction conditions and reactants. Reactions with penicillin G, 100 microliters of 1 mg/ml solution in water, were carried out and their light output recorded versus time, FIG. 2. When the peroxide used was hydrogen peroxide, 100 microliters of 0.018 M, at pH 11.0, the reaction produces a large amount of light quickly, curve D, but the light production decreases nearly as rapidly. If the peroxide added is tert-butyl hydroperoxide, 100 microliters of 0.02 M, the reaction produces much more light, curves E, F, and G, but not as rapidly. At pH 10.0, curve E, the peak light output is not reached until 18 minutes, while at pH 11.0, curve F, and pH 12.0, curve G, the peak is reached more rapidly, at 6 and 2 minutes, respectively, without appreciably decreasing the total light produced.

EXAMPLE 5

Figure 3A:
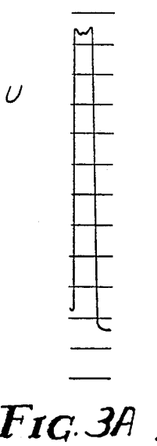
Figure 3B:
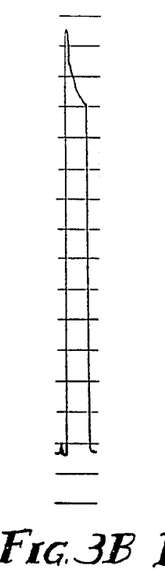
Figure 3C:
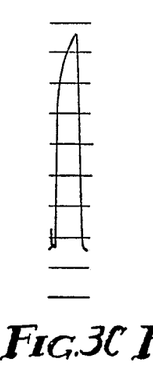
Figure 3D:
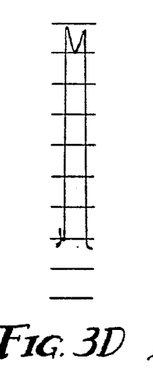
Figure 3E:
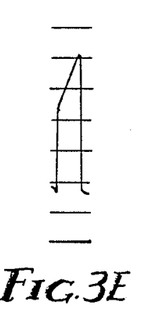

FIG. 3 shows 30-second traces recorded by a strip recorder coupled to the luminometer in Example 1 for penicillin G (FIG. 3A), penicillin V (FIG. 3B), ampicillin (FIG. 3C), aminopenicilloic acid (FIG. 3D) and cephalothin (FIG. 3E). These characteristic traces, different for each beta-lactam examined, serve as chemiluminescent fingerprints for the various beta-lactams and are useful as a qualitative analysis method.

EXAMPLE 6

A series of reactions were carried out with 100 microliters of luminol solution which contained 10 micrograms of luminol, 0.1% Tween® 20, 0.1 M sodium bicarbonate, and 0.005 M ethylenediaminetetraacetic acid pH 10.0), by adding 50 microliters of a solution containing 1 mg of a beta-lactam antibiotic per ml, and 50 microliters of one of bovine hemoglobin (Sigma) at $2.3 \times 10^{-7}$ mg per ml, microperoxidase (Sigma) at $2.6 \times 10^{-8}$ mg per ml, or water. To these solutions, 100 microliters of hydrogen peroxide solution, 0.018 M in 0.001 M ethylenediaminetetraacetic acid, or sodium perborate solution, 0.02 M in 0.002 M ethylenediaminetetraacetic acid, was injected in the dark as described in Example 1. The light produced from the reactions was observed and the results are shown in Tables III, IV and V.

TABLE III

Reactions of Beta-lactams and Luminol with a Hemoglobin Catalyst

| Beta-lactam | ELO Factor with $H_2O_2$ | ELO Factor with $NaBO_2.H_2O_2$ |
|---|---|---|
| Ampicillin | 24.4 | 21.7 |
| Cloxicillin | 11.1 | 10.1 |
| Penicillin G | 17.4 | 21.7 |
| Cephapirin | 10.2 | 24.9 |
| Cephalothin | 9.2 | 21.3 |

TABLE IV

Reactions of Beta-Lactams and Luminol with a Micro-Peroxidase Catalyst

| Beta-Lactam | ELO Factor with $H_2O_2$ | ELO Factor with $NaBO_2.H_2O_2$ |
|---|---|---|
| Ampicillin | 17.9 | 15.7 |
| Cloxicillin | 8.2 | 8.6 |
| Penicillin G | 15.5 | 17.2 |
| Cephapirin | 15.9 | 33.0 |
| Cephalothin | 11.8 | 20.4 |

TABLE V

Reactions of Beta-Lactams and Luminol with No Catalyst

| Beta-Lactam | ELO Factor with $H_2O_2$ | ELO Factor with $NaBO_2.H_2O_2$ |
|---|---|---|
| Ampicillin | 7.6 | 5.2 |
| Cloxicillin | 4.7 | 3.3 |
| Penicillin G | 6.2 | 5.0 |
| Cephapirin | 3.6 | 6.2 |
| Cephalothin | 3.6 | 5.2 |

These data indicate that the addition of beta-lactam antibiotics to luminol reactions with hemoglobin or micro-peroxidase catalysts produce a greater amount of light, and that, without a catalyst, the reaction also produces considerable light. Also, both hydrogen peroxide and sodium perborate are shown to be useful oxidizing agents for these reactions. In the case of cephalothin and cephapirin, the use of sodium perborate produces significantly more light than does hydrogen peroxide.

EXAMPLE 7

Test compounds were added to the reaction of penicillin G, 1 mg per ml in water, and sodium perborate, 0.02 M in 0.002 M ethylenediaminetetraacetic acid. Each compound was dissolved in 0.05 M sodium borate which was 0.005 M in ethylenediaminetetraacetic acid and contained 0.1% Tween® 20 at pH 9.5, with the exception of coumarin 2 and acridone which were dissolved in 0.5 ml of dimethyl sulfoxide and then diluted to 10.0 ml with the borate buffer. The reactions were run with 50 microliters of horseradish peroxidase as in Example 1, or with 50 microliters of buffer without catalyst. The reactions were initiated by combining the peroxide, 100 microliters of the test compound solution, and 50 microliters of penicillin G as in Example 1 and observing the light produced.

The results of these reactions are shown in Table VI as the ratio of the light produced with penicillin G present to the light produced without it. Among the compounds tested for chemiluminescent behavior according to this present invention, coumarin 2, sulforhodamine 101, 4-methylumbelliferone, umbelliferone, fluoresceinamine isomer II, fluorescein, luminol and iso-luminol act as useful chemiluminescent compounds for the beta-lactam reaction, and of these, iso-luminol and luminol are preferred. The remaining compounds listed in Table VI are not suitable for use in the practice of the present invention.

TABLE VI

Reaction of Penicillin G with Sodium Perborate in the Presence of Different Chemiluminescent Compounds

| Chemiluminescent Compound | Concentration (mg/ml) | ELO Factor with HRP* | ELO Factor with Buffer |
|---|---|---|---|
| Coumarin 2 | 0.07 | 2.0 | 1.6 |
| Sulforhodamine 101 | 0.1 | 5.7 | 3.3 |
| Sulforhodamine B | 0.09 | 1.2 | 1.2 |
| Acridone | 0.07 | 1.5 | 1.1 |

TABLE VI-continued

Reaction of Penicillin G with Sodium Perborate in the Presence of Different Chemiluminescent Compounds

| Chemiluminescent Compound | Concentration (mg/ml) | ELO Factor with HRP* | ELO Factor with Buffer |
|---|---|---|---|
| Dansyl Acid | 0.05 | 1.4 | 1.2 |
| 4-Methyl-Umbelliferone | 0.09 | 1.8 | 2.0 |
| Umbelliferone | 0.07 | 2.4 | 1.0 |
| Fluoresceinamine isomer II | 0.06 | 1.7 | 2.4 |
| Fluorescein | 0.1 | 2.2 | 1.7 |
| 3-Aminophthalic acid | 0.23 | 1.2 | 1.0 |
| iso-Luminol | 0.1 | 5.0 | 5.6 |
| Luminol | 0.1 | 4.3 | 5.7 |

*HRP = horseradish peroxidase

EXAMPLE 8

Buffers for chemiluminescent reactions affect the light produced from the beta-lactam reaction. The reactions were run in the buffers shown in Table VII by dissolving luminol at 0.01 mg per ml in the buffer solution which was 0.005 M in ethylenediaminetetraacetic acid and contained 0.1% Tween 20 (pH 9.5). To 100 microliters of these luminol solutions, 50 microliters of aqueous beta-lactam solution, 1 mg per ml, and 50 microliters of horseradish peroxidase, $6.8 \times 10^{-5}$ mg per ml, were added. The reaction was initiated by injection of hydrogen peroxide solution, 0.018 M in 0.001 M ethylenediaminetetraacetic acid as in Example 1.

The results of these reactions (Table VII) indicate that while there is an ELO in each of the buffers, carbonate, borate, and Tris buffers produce the largest ELO Factor for the beta-lactams tested.

TABLE VII

Effect of Buffers Upon the ELO of Beta-Lactams

| Beta-Lactam | Carbonate 0.1 M | Hepes 0.1 M | Phosphate 0.1 M | Tris 0.1 M | Glycine 0.1 M | Borate 0.05 M |
|---|---|---|---|---|---|---|
| Penicillin G | 17.7 | 2.3 | 3.4 | 4.0 | 2.6 | 4.7 |
| Penicillin V | 11.9 | 2.2 | 1.9 | 3.7 | 2.3 | 5.2 |
| Ampicillin | 33.4 | 14.8 | 5.1 | 8.4 | 9.6 | 9.4 |
| Cloxicillin | 9.4 | 3.5 | 1.7 | 4.4 | 7.8 | 3.3 |
| Aminopenicilloic Acid | 5.9 | 0.8 | 0.8 | 1.7 | 1.5 | 1.7 |
| Cephapirin | 4.9 | 0.0 | 0.0 | 0.2 | 0.0 | 1.9 |
| Cephalothin | 6.1 | 0.0 | 0.0 | 1.4 | 0.1 | 2.4 |

EXAMPLE 9

Luminol can also be detected by the beta-lactam reaction in the presence of a peroxide, but in the absence of an oxidation catalyst. Luminol solutions containing 0.1 mg/ml to 2.5 ng/ml were prepared by dilution in 0.1 M sodium bicarbonate buffer containing 0.005 M ethylenediaminetetraacetic acid and 0.1% Tween ® 20 (pH 10.0). To 100 microliters of each luminol solution, 50 microliters of water and 50 microliters of penicillin G solution, 1.0 mg/ml in water, were added. The chemiluminescent reaction was initiated by injecting 100 microliters of 0.018 M hydrogen peroxide in 0.001 M ethylenediaminetetraacetic acid solution. The light output of the reaction was observed as in Example 1 with the exception that here the light output was integrated over a 60 second period.

Figure 4:
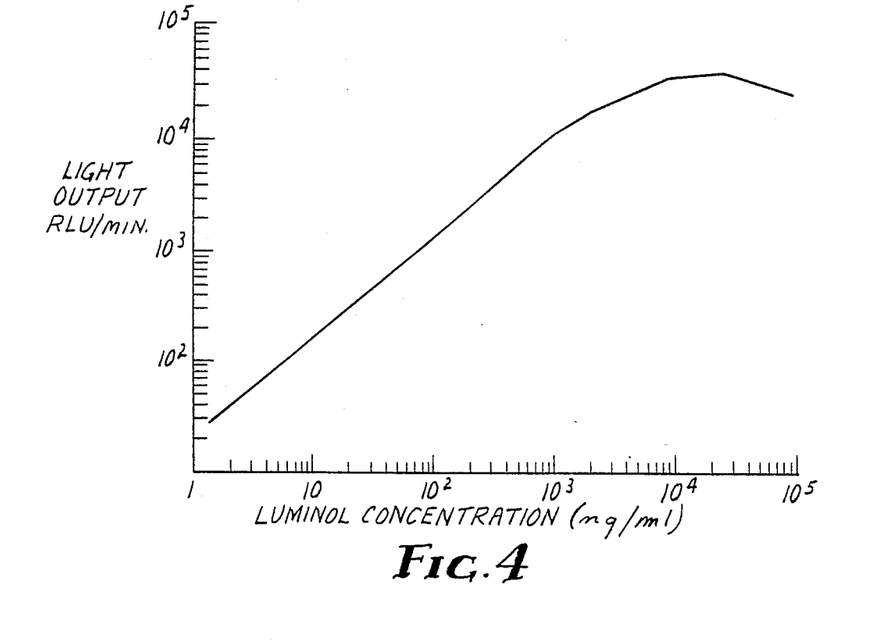

The results of this assay are shown in FIG. 4. The limit of detection under these conditions appears to be 1.5 ng of luminol per ml of solution ($8.5 \times 10^{-9}$ M).

EXAMPLE 10

The beta-lactam reaction can also be used to detect the presence of hydrogen peroxide. Hydrogen peroxide solutions were prepared by dilution in water from a concentration of 0.018 M to $1.8 \times 10^{-6}$ M. To a solution of 100 microliters of luminol solution containing 1 microgram/ml, 0.005 M ethylenediaminetetraacetic acid and 0.1% Tween 20 (pH 10.0) and 100 microliters of penicillin G solution, 1 mg/ml, 100 microliters of hydrogen peroxide solution was added and the light produced by the reaction observed for 60 seconds as in Example 8.

Figure 5:
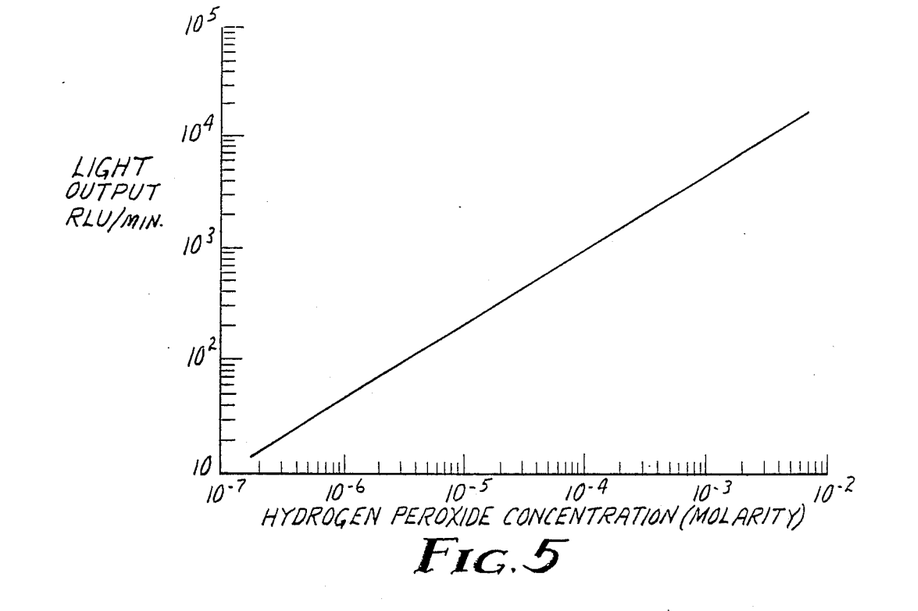

The results of the assay, shown in FIG. 5, indicate that hydrogen peroxide can be detected to a concentration of $3.7 \times 10^{-7}$ M.

EXAMPLE 11

Two different peroxides were used in place of hydrogen peroxide in the beta-lactam reaction. To a mixture of 100 microliters of luminol solution, 0.1 mg/ml in 0.1 M sodium bicarbonate, 0.005 M ethylenediaminetetraacetic acid, and 0.1% Tween 20 at pH 10.0 and 100 microliters of beta-lactam solution, 1 mg/ml in water, was added in the dark either 100 microliters of tert-butyl hydroperoxide (t-BuOOH), 0.02 M in 0.001 M ethylenediaminetetraacetic acid, or 100 microliters of meta-chloroperbenzoic acid (MCPB), 0.002 M in 0.001 M ethylenediaminetetraacetic acid, and the light produced by the reaction was integrated over a 1 minute period. The results of the reaction are reported in Table VIII as the ELO Factor.

TABLE VIII

Use of t-Butyl Hydroperoxide and m-Chloroperbenzoic Acid in the Beta-Lactam Reaction

| Beta-Lactam | ELO Factor | |
|---|---|---|
| | t-BuOOH | MCPB |
| Penicillin G | 92.7 | 17.7 |
| Ampicillin | 18.1 | 6.8 |
| Cloxicillin | 34.6 | 5.0 |
| Cephapirin | 91.6 | 3.5 |
| Cephalothin | 650.6 | 4.7 |

These results show that both of these peroxides produce significant amounts of light upon reaction with beta-lactams. The use of tert-butyl hydroperoxide is particularly effective in these reactions as can be seen by the high ELO Factors observed.

EXAMPLE 12

Figure 6:
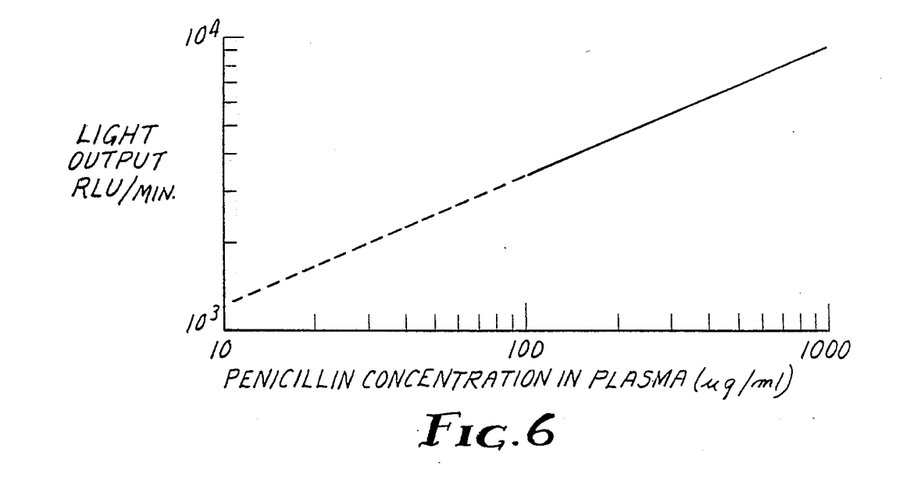
Figure 7:
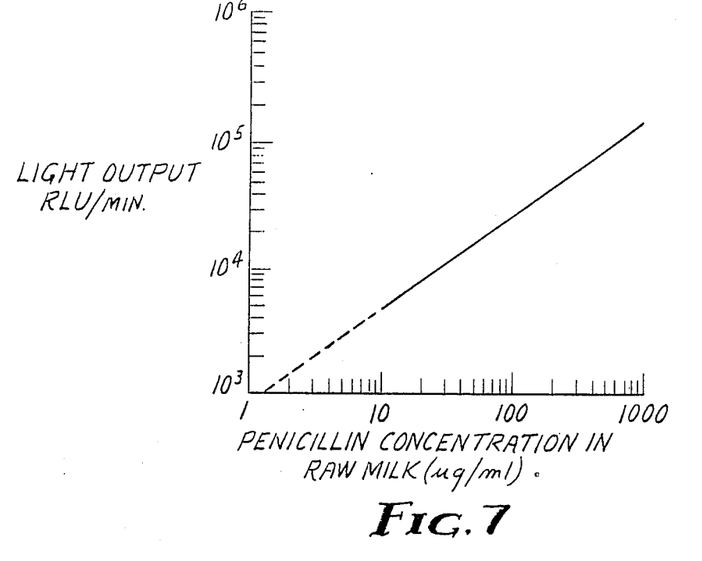

The beta-lactam reaction is useful in both blood plasma and milk. Reactions were carried out in the manner of Example 3 with penicillin G in water solution, 10 mg/ml, diluted tenfold with plasma or with raw milk, resulting in a final concentration of 1 mg of penicillin G per ml of solution. Further dilutions of the beta-lactam antibiotic were carried out with the appropriate fluid (i.e., either plasma or milk). To 50 microliters of plasma or milk were added 100 microliters of water and 100 microliters of a luminol solution containing 0.1 mg/ml of luminol, 0.1 M sodium bicarbonate, 0.005 M ethylenediaminetetraacetic acid, and 0.1% Tween ® 20. The reaction was initiated by injecting 100 microliters hydrogen peroxide solution, 0.018 M in 0.001 M ethylenediaminetetraacetic acid, in the dark, and the light from the reaction monitored for 60 seconds. From the plots shown in FIGS. 6 and 7 for blood plasma and milk, respectively, of the net light output versus the concentration of penicillin G present, it is seen that the light output from the beta-lactam reaction varies in a linear fashion with the concentration of penicillin G. This allows the detection and the quantitation of this antibiotic to levels of approximately 10 micrograms/ml in blood plasma and 1 microgram/ml in milk.

When the sample to be analyzed is milk, it is preferred for reasons of sensitivity that analysis of the reaction be commenced immediately (i.e., within about 10 seconds) after the components of the reaction system an the sample have been combined.

EXAMPLE 13

The beta-lactam reaction was carried out with 100 microliters of luminol solution, 1 microgram/ml in 0.1 M NaHCO3, 0.005 M ethylenediaminetetraacetic acid, and 0.1% Tween 20 at pH 10.0, 50 microliters of penicillin G in water, 1 mg/ml, and 100 microliters of hydrogen peroxide, 0.018 M, 0.001 M ethylenediaminetetraacetic acid. This reaction was modified by the addition of 50 microliters of either sodium cyanide, 2.6 mg/ml, or sodium azide, 2.8 mg/ml.

Figure 8:
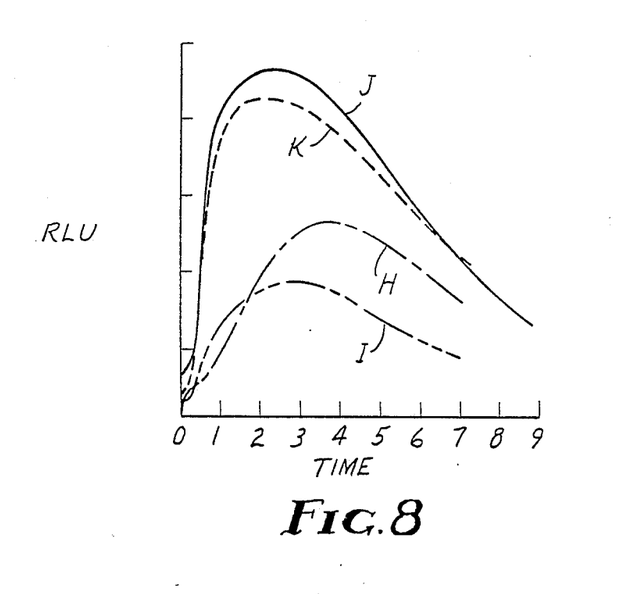

The light produced by these reactions was monitored on a strip chart recorder, reproduced in FIG. 8, and integrated every minute for five minutes. The results, shown in Table IX, indicate that the addition of azide significantly increases the light produced by the reaction, 185% of that without it. While cyanide decreases the light output (about a 30% decrease over the five minute observation), when used in combination with azide the light output is about the same as that with azide alone or 174% of the unmodified reaction. One other result which should be noted is that the peak light output is achieved more quickly when azide and/or cyanide ions are present than when they are absent (FIG. 8).

TABLE IX

| | Effects of Added Cyanide and Azide Ions Upon the Penicillin G Reaction | | | | | |
|---|---|---|---|---|---|---|
| Ion | Integrated Light Output ($\times 10^{-3}$) | | | | | |
| Added | t = 1 | 2 | 3 | 4 | 5 | Total |
| None (Curve H of FIG. 8) | 28 | 76 | 118 | 128 | 117 | 467 |
| Sodium cyanide (Curve I of FIG. 8) | 28 | 68 | 83 | 79 | 66 | 324 |
| Sodium azide (Curve J of FIG. 8) | 78 | 196 | 213 | 203 | 177 | 867 |
| Sodium cyanide and Sodium azide (Curve K of FIG. 8) | 63 | 190 | 201 | 190 | 168 | 812 |

EXAMPLE 14

The beta-lactam reaction was run as in Example 13 using penicillin G and either sodium azide alone or a sodium azide/sodium cyanide mixture, and compared to a background reaction without penicillin G. The ratios of the integrated light outputs at 30 and 60 seconds of reaction are shown in Table X and indicate a considerable increase, 1.9 and 10.5 fold, respectively, with sodium azide, and 1.1 and 3.1 fold, respectively, with sodium azide and sodium cyanide.

TABLE X

| | Effect Upon ELO Factors | |
|---|---|---|
| Ion | ELO Factor | |
| Added | t = 30 seconds | 60 seconds |
| None | 3.4 | 6.0 |
| Sodium azide | 6.5 | 63.0 |
| Sodium cyanide and Sodium azide | 3.8 | 19.0 |

EXAMPLE 15

The beta-lactam reaction was again run as in Example 13 using penicillin G and, this time, sodium ascorbate, 300 ng/ml, or a mixture of sodium ascorbate, 300 ng/ml, and sodium azide, 2.8 mg/ml. The light output of the reactions was not affected significantly, but the background light output was considerably reduced. This can be seen by the ELO Factors for these reactions shown in Table XI, the ELO Factors increasing to over 200 after two minutes of reaction.

TABLE XI

| | Effect of Ascorbate Upon the ELO Factor | | | |
|---|---|---|---|---|
| Ion | ELO Factor | | | |
| Added | t = 30 | 60 | 90 | 120 seconds |
| None | 3.4 | 6.0 | — | — |
| Sodium Ascorbate | 9.8 | 26.4 | 66.3 | — |
| Sodium Ascorbate and Sodium Azide | 12.3 | 72.3 | 114.1 | 201.1 |

EXAMPLE 16

Figure 9:
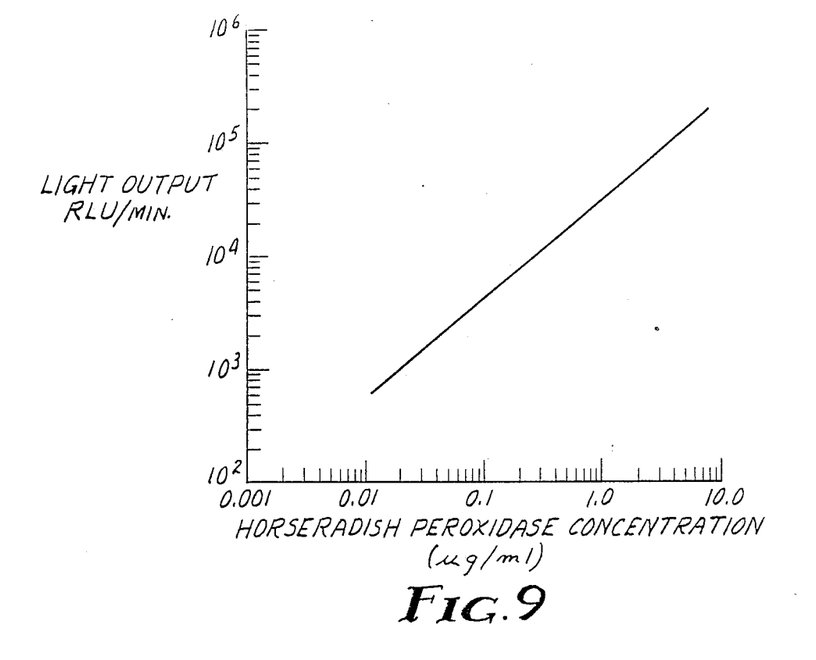

Luminol reaction oxidation catalysts can be detected and quantitated with the beta-lactam reaction. To a mixture of 100 microliters of luminol solution, 1 mg/ml, in 0.1 M sodium bicarbonate, 0.005 M ethylenediaminetetraacetic acid, and 0.1% Tween ® 20 at pH 10.0, 50 microliters of penicillin G solution, 0.2 mg/ml in water, and 50 microliters of horseradish peroxidase solution, diluted with buffer from 5600 to 14 ng/ml, was added 100 microliters of hydrogen peroxide, 0.018 M, in the dark and the light produced by the reaction was monitored for 10 seconds. The net light output of the reactions was plotted versus the concentration of catalyst in FIG. 9 and demonstrates that a linear relationship exists between them. This results in a detection limit of 6 ng/ml under these conditions

What is claimed is:

1. In a method of assay for the detection or quantification of a component of a chemiluminescent reaction, said chemiluminescent reaction involving a chemiluminescent compound and a peroxide source, said component to be detected or quantified being one of said chemiluminescent compound, said peroxide source, and an oxidation catalyst which participates in the chemiluminescent reaction, the improvement comprising the inclusion of a beta-lactam and a base in said assay, said base being present in an amount such that said assay is carried out at a basic pH, and wherein said beta-lactam is present in an amount sufficient to enhance the light output of said chemiluminescent reaction and thereby enhance the sensitivity of said assay for the detection or quantification of said component of said chemiluminescent reaction.

2. A method according to claim 1, wherein said component being detected or quantified is said oxidation catalyst.

3. A method according to claim 2, wherein said oxidation catalyst is a peroxidase.

4. A method according to claim 1, wherein said component being detected or quantified is said peroxide source.

5. A method according to claim 4, wherein said peroxide source is hydrogen peroxide.

6. A method according to claim 1, wherein said component being detected or quantified is said chemiluminescent compound.

7. A method according to claim 6, wherein said chemiluminescent compound is selected from the group consisting of luminol, a luminol analog, isoluminol and an isoluminol analog.

* * * * *